United States Patent
Joy et al.

(10) Patent No.: US 7,163,966 B2
(45) Date of Patent: Jan. 16, 2007

(54) SUPERABSORBENT POLYMER HAVING INCREASED RATE OF WATER ABSORPTION

(75) Inventors: Mark C. Joy, Greensboro, NC (US); Whei-Neen Hsu, Greensboro, NC (US)

(73) Assignee: Stockhausen, Inc., Greensboro, NC (US)

( * ) Notice: Subject to any disclaimer, the term of this patent is extended or adjusted under 35 U.S.C. 154(b) by 170 days.

(21) Appl. No.: 10/741,271

(22) Filed: Dec. 19, 2003

(65) Prior Publication Data

US 2005/0137546 A1 Jun. 23, 2005

(51) Int. Cl.
*C08J 9/08* (2006.01)
*C08F 20/02* (2006.01)

(52) U.S. Cl. ......... 521/72; 521/142; 524/729; 523/105; 523/132; 523/173; 525/329.7; 525/330.2

(58) Field of Classification Search ......... 521/72, 521/148; 524/729; 523/105, 132, 173; 525/329.7, 525/330.2
See application file for complete search history.

(56) References Cited

U.S. PATENT DOCUMENTS

| | | |
|---|---|---|
| 5,118,719 A | 6/1992 | Lind |
| 5,154,713 A | 10/1992 | Lind |
| 5,236,965 A | 8/1993 | Engelhardt et al. |
| 5,314,420 A | 5/1994 | Smith et al. |
| 5,399,591 A | 3/1995 | Smith et al. |
| 5,409,771 A | 4/1995 | Dahmen et al. |
| 5,451,613 A | 9/1995 | Smith et al. |
| 5,712,316 A * | 1/1998 | Dahmen et al. ............ 521/72 |
| 6,136,873 A | 10/2000 | Hahnle et al. |
| 6,441,266 B1 | 8/2002 | Dyer et al. |
| 6,562,879 B1 | 5/2003 | Hatsuda et al. |
| 2002/0039869 A1 | 4/2002 | Achille |
| 2003/0118821 A1 | 6/2003 | Sun et al. |

FOREIGN PATENT DOCUMENTS

WO  WO 98/47454 A  10/1998

* cited by examiner

*Primary Examiner*—Robert D. Harlan
(74) *Attorney, Agent, or Firm*—Smith Moore LLP

(57) ABSTRACT

The invention relates to a superabsorbent polymer wherein an increased rate of water absorption is obtained by the addition of an encapsulated blowing agent. The invention relates to a superabsorbent polymer including an encapsulating blowing agent and having a vortex time of 40 seconds or less. In particular, the superabsorbent polymer includes from about 55 to about 99.9 wt. % of polymerizable unsaturated acid group containing monomers; from about 0.001 to about 5.0 wt. % of internal crosslinking agent; wherein the wherein the composition has a degree of neutralization of more than about 20%; and from about 0.05 to about 10.0 wt. % of an encapsulated blowing agent.

19 Claims, No Drawings

SUPERABSORBENT POLYMER HAVING INCREASED RATE OF WATER ABSORPTION

FIELD OF THE INVENTION

The invention relates to superabsorbent polymers which absorb water, aqueous liquids and blood wherein the superabsorbent polymers of the present invention have improved properties, in particular faster absorption time while maintaining acceptable fluid retention properties and absorbency under load. The present invention also relates to preparation of these superabsorbent polymers and their use as absorbents in hygiene articles and in industrial fields.

BACKGROUND OF THE INVENTION

Superabsorbent refers to a water-swellable, water-insoluble, organic or inorganic material capable of absorbing at least about 10 times its weight and up to about 30 times its weight in an aqueous solution containing 0.9 weight percent sodium chloride solution in water. A superabsorbent polymer is a crosslinked neutralized polymer which is capable of absorbing large amounts of aqueous liquids and body fluids, such as urine or blood, with swelling and the formation of hydrogels, and of retaining them under a certain pressure in accordance with the general definition of superabsorbent.

The superabsorbent polymers that are currently commercially available are crosslinked polyacrylic acids or crosslinked starch-acrylic acid graft polymers, in which some of the carboxyl groups are neutralized with sodium hydroxide solution or potassium hydroxide solution. As a result of these characteristic properties, these polymers are chiefly used for incorporation into sanitary articles, such as babies' diapers, incontinence products and sanitary towels.

For fit, comfort and aesthetic reasons and from environmental aspects, there is an increasing trend to make sanitary articles smaller and thinner. This is being accomplished by reducing the content of the high volume fluff fiber of these articles. To ensure a constant total retention capacity of body fluids in the sanitary articles, more superabsorbent polymer content is being used in these sanitary articles. As a result of this, superabsorbent polymers must have increased absorption speed characteristics while retaining other characteristics such as adequate absorption under load and retention capacity.

In future diaper constructions, it is expected there will be less fiber material, or potentially none at all, in the absorber layer to assist in transportation of the liquid or maintenance of an open, fluid permeable structure. The superabsorbent polymer of these future diaper constructions must have a sufficiently high stability in the swollen state, generally called gel strength, so the swollen gel has a sufficient amount of capillary spaces through which liquid can be transported. In addition, the superabsorbent polymers in such diapers must also have a higher absorption rate to maximize the use of available capillary spaces and to compensate for the reduction of typically fast absorbing fibers.

It is therefore an object of the present invention to provide an absorbing polymer composition that exhibits increased rate of water absorption as well as maintaining excellent properties. It is an object to maintain high absorption under load and liquid retention even when the superabsorbent polymer is increased in percent by weight based on the absorbent structure. This can be achieved by increasing the absorption rate of the superabsorbent polymer by increasing the microcellular structure of the polymer.

SUMMARY OF THE INVENTION

The present invention is directed to a superabsorbent polymer comprising an encapsulated blowing agent and having a vortex time of 40 seconds or less.

The present invention is also directed to a superabsorbent polymer comprising a) from about 55 to about 99.9 wt. % of polymerizable unsaturated acid group containing monomers; b) from about 0.001 to about 5.0 wt. % of internal crosslinking agent; wherein the composition has a degree of neutralization of more than about 20 mol %; and c) from about 0.05 to about 5.0 wt. % of an encapsulated blowing agent.

In addition, the present invention is directed to a method of preparing superabsorbent polymers comprising the steps of a) dissolving at least one acrylic acid monomer and/or its sodium salt and a cross-linking agent in an aqueous solution to form a monomer solution; b) adding to the monomer solution, an encapsulated blowing agent in sufficient amount to form, when polymerized a microcellular expanded hydrogel; and c) initiating free radical polymerization by adding to the monomer solution either immediately before or immediately after, or simultaneously with the addition of the encapsulated blowing agent, an effective amount of at least one free radical initiator and polymerizing at temperatures ranging from about 0° C. to about 130° C.

DESCRIPTION OF THE PREFERRED EMBODIMENTS

A suitable superabsorbent polymer may be selected from natural, biodegradable, synthetic and modified natural polymers and materials. The term crosslinked used in reference to the superabsorbent polymer refers to any means for effectively rendering normally water-soluble materials substantially water-insoluble but swellable. Such a crosslinking means can include for example, physical entanglement, crystalline domains, covalent bonds, ionic complexes and associations, hydrophilic associations such as hydrogen bonding, hydrophobic associations or Van der Waals forces. Superabsorbent polymers include internal crosslinking and surface crosslinking.

Specifically, applicants have discovered a superabsorbent polymer having an increased rate of water absorption is obtained by the addition of an encapsulated blowing agent.

One embodiment of the present invention is directed to a hydrophilic superabsorbent comprising a) from about 55 to about 99.9 wt. % of polymerizable unsaturated acid group containing monomers; b) from about 0.001 to about 5.0 wt. % of internal crosslinking agent; wherein the composition has a degree of neutralization of more than about 20 mol %; and c) from about 0.05 to about 5.0 wt. % of an encapsulated blowing agent.

The superabsorbent polymer of the present invention is obtained by the initial polymerization of from about 55 to about 99.9 wt. % of polymerizable unsaturated acid group containing monomers. Suitable monomers include those containing carboxyl groups, such as acrylic acid, methacrylic acid or 2-acrylamido-2-methylpropanesulfonic acid, or mixtures of these monomers are preferred here. It is preferable for at least about 50-wt. %, and more preferably at least about 75 wt. % of the acid groups to be carboxyl groups. The acid groups are neutralized to the extent of at least about 25 mol %, preferably 25 mol % to 80 mol %, that is the acid groups are present in salt form. It is preferred to obtain polymers obtained by polymerization of acrylic acid or methacrylic acid, the carboxyl groups of which are neutralized to the extent of 50–80-mol %, in the presence of internal crosslinking agents.

Other monomers, which can be used for the preparation of the superabsorbent polymers according to the invention, are from 0 to about 40 wt. % of ethylenically unsaturated monomers which can be copolymerized with a), such as e.g. acrylamide, methacrylamide, hydroxyethyl acrylate, dimethylaminoalkyl (meth)-acrylate, ethoxylated (meth)-acrylates, dimethylaminopropylacrylamide or acrylamidopropyltrimethylammonium chloride. Including more than 40 wt. % of these monomers may impair the swellability of the superabsorbent polymers.

The internal crosslinking agent may have at least two ethylenically unsaturated double bonds or one ethylenically unsaturated double bond and one functional group which is reactive towards acid groups of the polymerizable unsaturated acid group containing monomers or several functional groups which are reactive towards acid groups can be used as the internal crosslinking component and which is present during the polymerization of the polymerizable unsaturated acid group containing monomers.

Examples of internal crosslinking agents used in superabsorbent polymers of the present invention include aliphatic unsaturated amides, such as methylenebisacryl- or -methacrylamide or ethylenebisacrylamide, and aliphatic esters of polyols or alkoxylated polyols with ethylenically unsaturated acids, such as di(meth)acrylates or tri(meth) acrylates of butanediol or ethylene glycol, polyglycols or trimethylolpropane, di- and triacrylate esters of trimethylolpropane which is preferably oxyalkylated, preferably ethoxylated, with about 1 to about 30 mol of alkylene oxide, acrylate and methacrylate esters of glycerol and pentaerythritol and of glycerol and pentaerythritol oxyethylated with preferably about 1 to about 30 mol of ethylene oxide and furthermore allyl compounds, such as allyl (meth)acrylate, alkoxylated allyl (meth)acrylate reacted with preferably 1 to 30 mol of ethylene oxide, triallyl cyanurate, triallyl isocyanurate, maleic acid diallyl ester, poly-allyl esters, tetraallyloxyethane, triallylamine, tetraallylethylenediamine, diols, polyols, hydroxy allyl or acrylate compounds and allyl esters of phosphoric acid or phosphorous acid, and furthermore monomers which are capable of crosslinking, such as N-methylol compounds of unsaturated amides, such as of methacrylamide or acrylamide, and the ethers derived there from. Ionic crosslinkers, such as multivalent metal salts, may also be used in the present invention. Mixtures of the crosslinking agents mentioned may also be employed. The content of the internal crosslinking agents is from about 0.01 to about 5 wt. %, and preferably from about 0.1 to about 3.0 wt. %, based on the total amount of the polymerizable unsaturated acid group containing monomers.

The encapsulated blowing agents may include any carbonate or bicarbonate containing salt, or mixed salt, sodium carbonate, potassium carbonate, ammonium carbonate, magnesium carbonate, or magnesium (hydroxic) carbonates, calcium carbonate, barium carbonate, bicarbonates and hydrates of these, azo compounds or other cations, as well as naturally occurring carbonates, such as dolomite, or mixtures thereof. Blowing agents may include carbonate salts of multi-valent cations, such as Mg, Ca, Zn, and the like. Although certain of the multi-valent transition metal cations may be used, some of them, such as ferric cation, can cause color staining and may be subject to reduction-oxidation reactions or hydrolysis equilibria in water. This may lead to difficulties in quality control of the final polymeric product. Also, other multi-valent cations, such as Ni, Ba, Cd, Hg would be unacceptable because of potential toxic or skin sensitizing effects. A preferred blowing agent is $MgCO_3$, which may also be represented by the formula; $(MgCO_3)_4 \cdot Mg(OH)_2 \cdot 5H_2O$. Another preferred blowing agent is $(NH_4)_2CO_3$. The blowing agents $MgCO_3$ and $(NH_4)_2CO_3$ may also be used in mixtures.

Encapsulation of such blowing agents provide a controllable delayed release of a gas such as carbon dioxide when dispersed in a monomer solution that is heated or polymerized in accordance with the present invention. The method for encapsulation comprises coating a particular blowing agent with a resin preferably diluted in a solvent solution. The solvent utilized may be an organic or inorganic solvent such as water depending on the nature of the coating to be applied. A second coating, generally called a sealing coating, may be applied on the encapsulated blowing agent.

Resins employed in encapsulating the blowing agent in the superabsorbent polymers of the present invention may include but are not limited to natural and synthetic resins, polyolefins (for example, polyethylene and polypropylene), olefin copolymers (for example, copolymers of ethylene and ethylvinylacetate), polyaromatic olefins, styrenic compounds and polymerized halo-diolefins (for example, neoprene, ethylene-propylene copolymers, polyvinyl chloride, polyvinyl alcohol, polyvinyl acetate, polyacrylic acid derivatives, polycarbonate, polyesters, poly-alpha methylstyrene and polystyrene), starch, gelatin and cellulose. Preferred resin materials include polyols such as polyethylene glycol.

From 0 and about 95% by weight of the appropriate solvent is added to the resin to form a solution and coated on to the blowing agent. Resin solution is applied on the blowing agent in an amount from about 10% and about 80% by weight of the encapsulation compound, preferably from about 30% to about 70% by weight of the encapsulation compound and can be applied with any encapsulating method commonly employed in the art including, but not limited to, tumbling or spraying. The purpose of the encapsulating resin is to delay the gas release by the blowing agent in the monomer solution until a later stage of the polymerization process, allowing control of and improving the microcellular structure of the hydrogel.

The encapsulation of the blowing agent by the resinous substrate can be accomplished at room temperature but elevated temperatures are preferred. Preferably, the resinous substrate is about 30 to about 70% by weight of the encapsulated compound.

It is preferred to add from about 0.05 to about 10 wt. % of the encapsulated blowing agent (based on the total monomer solution weight) in the monomer solution. It is most preferred to add from about 0.2 wt. % to about 5 wt. % of the encapsulated blowing agent to the monomer solution. The encapsulated blowing agents should be added prior to, simultaneously with or immediately after polymerization is initiated. The encapsulated blowing agents are not as effective if added after the hydrogel is formed, nor is it effective added after chopping or drying the gelled polymer. By varying the amount of the encapsulating resin and encapsulated blowing agent, the release of the blowing agent can be timed to provide the most advantageous microcellular structure of the resulting hydrogel.

The usual polymerization initiators, such as azo or peroxo compounds, redox systems or UV initiators, sensitizers, and/or radiation are used for initiation of the free-radical polymerization.

The superabsorbent polymers are typically surface crosslinked after polymerization. Surface crosslinking is a process that increases the crosslink density of the polymer matrix in the vicinity of the superabsorbent particle surface with respect to the crosslinking density of the particle interior. The superabsorbent polymers are typically surface crosslinked by the addition of a surface crosslinking agent. Preferred surface crosslinking agents include chemicals with one or more functional groups, which are reactive towards pendant groups of the polymer chains, typically the acid groups. The content of the surface crosslinking agents is from about 0.01 to about 5 wt. %, and preferably from about 0.1 to about 3.0 wt. %, based on the weight of the dry polymer. A heating step is preferred after addition of the surface crosslinking agent.

The superabsorbent polymers according to the invention can comprise include from 0 to about 5 wt. % of a multivalent metal salt, based on the weight of the mixture, on the surface of the polymer. The multivalent metal salt is preferably water-soluble. Examples of preferred metal cations include the cations of Al, Fe, Zr, Mg and Zn. Preferably, the metal cation has a valence of at least +3, with Al being most preferred. Examples of preferred anions in the multivalent metal salt include halides, chlorohydrates, sulfates, nitrates and acetates, with chlorides, sulfates, chlorohydrates and acetates being preferred, chlorohydrates and sulfates being more preferred and sulfates being the most preferred. Aluminum sulfate is the most preferred multivalent metal salt and is readily commercially available. The preferred form of aluminum sulfate is hydrated aluminum sulfate, preferably aluminum sulfate having from 12 to 14 waters of hydration. Mixtures of multivalent metal salts can be employed.

The polymer and multivalent metal salt suitably are mixed by dry blending, or preferably in solution, using means well known to those skilled in the art. Aqueous solutions are preferred. With dry blending, a binder may be employed in an amount sufficient to ensure that a substantially uniform mixture of the salt and the superabsorbent polymer is maintained. The binder may be water or a nonvolatile organic compound having a boiling point of at least 150° C. Examples of binders include water, polyols such as propylene glycol, glycerin and poly(ethylene glycol).

The superabsorbent polymer according to the invention may also include the addition of from 0 to about 5 wt. % of a surfactant to the polymer particle surface. It is preferred that these be added immediately prior to, during or immediately after the surface crosslinking step.

Examples of such surfactants include anionic, non-ionic, cationic and amphoteric surface active agents, such as fatty acid salts, coco amines and amides and their salts, alkylsulfuric ester salts, alkylbenzene sulfonic acid salts, dialkyl sulfo-succinate, alkyl phosphate salt, and polyoxyethylene alkyl sulfate salt; polyoxyethylene alkyl ether, polyoxyethylene alkyl phenol ether, polyoxyethylene fatty acid ester, sorbitan fatty acid ester, polyoxy sorbitan fatty acid ester, polyoxyethylene alkylamine, fatty acid esters, and oxyethylene-oxypropylene block polymer; alkyl amine salts, quaternary ammonium salts; and lauryl dimethylamine oxide. However, it is not necessary to restrict the surfactant to those mentioned above. Such surfactants may be used individually, or in combination.

The superabsorbent polymers may also include from 0 to about 30 wt. % of water-soluble polymers, such as partly or completely hydrolyzed polyvinyl acetate, polyvinylpyrrolidone, starch or starch derivatives, polyglycols or polyacrylic acids, preferably in polymerized-in form. The molecular weight of these polymers is not critical as long as they are water-soluble. Preferred water-soluble polymers are starch and polyvinyl alcohol. The preferred content of such water-soluble polymers in the superabsorbent polymer according to the invention is 0–30 wt. %, preferably 0–5 wt. %, based on the total amount of components. The water-soluble polymers, preferably synthetic polymers, such as polyvinyl alcohol, can also serve as a graft base for the monomers to be polymerized.

Further additives of the superabsorbent polymers according to the invention may optionally be employed, such as odor-binding substances, such as cyclodextrins, zeolites, inorganic or organic salts and similar materials; anti-caking additives, flow modification agents and the like.

The polymers according to the invention are preferably prepared by two methods. The polymers can be prepared continuously or discontinuously in a large-scale industrial manner by the abovementioned known process, the addition of the encapsulated blowing agent added immediately before, simultaneously with or after the initiation of polymer according to the invention being carried out accordingly.

According to the first method, the partially neutralized monomer, preferably acrylic acid, is converted into a gel by free-radical polymerization in aqueous solution in the presence of crosslinking agents and optionally further components, and the gel is comminuted, dried, ground and sieved off to the desired particle size. This solution polymerization can be carried out continuously or discontinuously.

A microcellular hydrogel is created as polymerization occurs because of the decomposition of the encapsulated blowing agent upon heating and/or a chemical reaction disperses gas bubbles throughout the hydrogel. The microcellular structure of the core polymer may appear cloudy (demonstrating relatively small dispersed gas bubbles), opaque (normally representing somewhat larger gas bubbles or higher quantities of carbon dioxide), or foamy. The microcellular gel volume increases range from about 1.0 to at least 10.0 times the volume of the monomer solution, primarily depending upon the degree of encapsulation and the concentration of the encapsulated blowing agent contained in the monomer solution.

In one embodiment, the superabsorbent polymer is used in the form of discrete particles. Superabsorbent polymer particles can be of any suitable shape, for example, spiral or semi-spiral, cubic, rod-like, polyhedral etc. Particle shapes having a large greatest dimension/smallest dimension ratio, like needles, flakes or fibers are also contemplated for use herein. Conglomerates of particles of superabsorbent polymers may also be used.

The superabsorbent polymer of the present invention may be characterized by its properties. In particular, the superabsorbent polymer of the present invention has a vortex time of about 40 seconds or less, preferably about 35 seconds or less. In addition the superabsorbent polymer of the present invention has an absorbency under load at 0.9 psi (AUL(0.9 psi)) of about 10 g/g or more, preferably, about 19 g/g or more. The capacity of the superabsorbent polymer as measured by the tea bag retention is about 20 g/g or more. In one embodiment of the present invention, the superabsorbent polymer has a vortex of 40 seconds or less, a AUL(0.9 psi) of 10 g/g or more and a capacity of about 20 g/g or more.

While particles are used by way of example of the physical form of superabsorbent polymers, the invention is not limited to this form and is applicable to other forms such as fibers, foams, films, beads, rods and the like.

The superabsorbent polymers of the present invention may be used in absorbent articles such as diapers and coatings. The present invention is directed generally to absorbent structures having enhanced liquid intake performance characteristics, and more particularly to absorbent structures having an enhanced intake rate upon repeated liquid insults thereof. For example, possible uses include incorporation into a disposable or otherwise absorbent article for absorbing various liquid body exudates. Such articles are well known and can include, without limitation, feminine care pads, interlabial products, tampons, diapers, incontinence articles, training pants, bed pads, sweat absorbing pads, shoe pads, bandages, helmet liners, wipes, etc. As another example, the absorbent structure may be useful by itself, such as in the form of a tissue, towel, napkin or the like.

TEST METHODS

Unless otherwise stated, the test fluid used in all the test methods described below is an aqueous 0.9 wt. % sodium chloride solution, such as that available from Ricca Chemical Company (Arlington, Tex.). Unless otherwise stated, all tests were conducted at about 70° F. and between 10 and 60% relative humidity.

Vortex Time

The vortex test measures the amount of time in seconds required for 2 grams of a superabsorbent material to close a vortex created by stirring 50 milliliters of saline solution at 600 revolutions per minute on a magnetic stir plate. The time it takes for the vortex to close is an indication of the free swell absorbing rate of the superabsorbent material.

Equipment and Materials
1. Schott Duran 100 ml Beaker and 50 ml graduated cylinder.
2. Programmable magnetic stir plate, capable of providing 600 revolutions per minute (such as that commercially available from PMC Industries, under the trade designation Dataplate® Model #721).
3. Magnetic stir bar without rings, 7.9 millimeters·times·32 millimeters, Teflon® covered (such as that commercially available from Baxter Diagnostics, under the trade designation S/PRIM. brand single pack round stirring bars with removable pivot ring).
4. Stopwatch
5. Balance, accurate to +/−0.01 g
6. Saline solution, 0.87 w/w % Blood Bank Saline available from Baxter Diagnostics (considered, for the purposes of this application to be the equivalent of 0.9 wt. % saline
7. Weighing paper
8. Room with standard condition atmosphere: Temp=23° C. +/−1° C. and Relative Humidity=50% +/−2%.

Test Procedure
1. Measure 50ml +/−0.01 ml of saline solution into the 100 ml beaker.
2. Place the magnetic stir bar into the beaker.
3. Program the magnetic stir plate to 600 revolutions per minute.
4. Place the beaker on the center of the magnetic stir plate such that the magnetic stir bar is activated. The bottom of the vortex should be near the top of the stir bar.
5. Weigh out 2 g +/−0.01 g of the superabsorbent material to be tested on weighing paper. NOTE: The superabsorbent material is tested as received (i.e. as it would go into an absorbent composite such as those described herein). No screening to a specific particle size is done, though the particle size is known to have an effect on this test.
6. While the saline solution is being stirred, quickly pour the superabsorbent material to be tested into the saline solution and start the stopwatch. The superabsorbent material to be tested should be added to the saline solution between the center of the vortex and the side of the beaker.
7. Stop the stopwatch when the surface of the saline solution becomes flat and record the time.
8. The time, recorded in seconds, is reported as the Vortex Time.

Tea Bag Retention (TB Retention)

The retention values were determined by performing a tea bag test. The test solution used was a 0.9% strength NaCl solution. 0.20 g of the test substance (screened between about 150 μm and about 850 μm) were sealed into a tea bag and immersed in the test solution for 30 minutes. The tea bag was subsequently spun in a centrifuge, for example, a commercially available laundry spin dryer, at 1600 rpm for 3 minutes. The amount of liquid absorbed was determined gravimetrically after subtraction of the blank value (weight of an empty tea bag after spinning) and converted to 1 g of test substance. The tea bag retention value corresponds to the amount of liquid absorbed in g/g of test substance.

Absorbency Under Load (AUL)

The ability of a superabsorbent material to absorb a liquid while under a load is determined as follows. A Demand Absorbency Tester (DAT) is used, which is similar to the GATS (Gravimetric Absorbency Test System), available from MIK Systems, Danners, Mass., as well as the system described by Lichstein at pages 129–142 of the INDA Technological Symposium Proceedings, March 1974. A porous plate is used, having ports confined within a 2.5 centimeter diameter area and covered by the Absorbency Under Load (AUL) apparatus. An electrobalance is used to measure the flow of fluid into the superabsorbent particles. For this test, the fluid employed is an aqueous solution containing 0.9 wt. % sodium chloride used at room temperature (approximately 23° C.)

The special AUL apparatus used to contain the superabsorbent particles comprises a cylinder made from 1 inch (2.54 centimeters) inside diameter thermoplastic tubing, which is machined-out slightly to be sure of concentricity. A 100 mesh stainless steel wire cloth is adhered on the bottom of cylinder by means of an adhesive. Alternatively, the stainless steel wire cloth can be fused to the bottom of cylinder by heating the wire cloth in a flame until red hot, after which the cylinder is, held onto the cloth until cooled. A soldering iron can be used to touch up the seal if unsuccessful or if it breaks. Care must be taken to maintain a flat, smooth bottom, and not distort the inside of the cylinder. A 4.4 gram piston is made from 1 inch diameter solid material (e.g., PLEXIGLAS) and is machined to closely fit without binding in the cylinder. The piston is used to provide the restraining load of 0.01 pound per square inch. A weight is used to provide the greater degrees of restraining load. As discussed above, the greater restraining loads are 0.29 pound per square inch, 0.57 pound per square inch, and 0.90 pound per square inch. Accordingly, a 100, 200, and 317 gram weight is used to provide the respective restraining loads (in addition to the 4.4 gram piston). A sample of superabsorbent particles weighing 0.160 (+/−0.005) gram is utilized for testing AUL. The sample is taken from granules which are pre-screened through U.S. standard 30 mesh and retained on U.S. standard 50 mesh (300–600 microns). The particles, when tested, have a moisture content of less than about 5 weight percent.

This test is initiated by placing a 3 centimeter diameter GF/A glass filter paper 130 onto the plate. The paper is sized to be larger than the internal diameter and smaller than the outside diameter of the cylinder to ensure good contact while eliminating evaporation over the ports of the DAT and then allowing saturation to occur. The particles are weighed on weighing paper and placed on the wire cloth at the bottom of the AUL apparatus. The apparatus is shaken to level the particles on the wire cloth. Care is taken to be sure no particles are clinging to the wall of the cylinder. After carefully placing, without pressing, the piston and, optionally, weight on the particles in the cylinder, the AUL apparatus is placed on the glass filter paper. The amount (in grams) of fluid picked up is monitored as a function of time either directly by hand, with a strip-chart recorder, or directly into a data acquisition or personal computer system.

The amount (in grams) of fluid picked up after 60 minutes, divided by the weight of the sample (0.160 gram) is the AUL value in grams of fluid picked up per gram of sample (g/g). The rate of fluid picked up can also be measured. Two checks can be made to ensure the accuracy of the instantaneous final readout. First, the height the piston rises, multiplied by the cross-sectional area of the cylinder should equal the volume of fluid picked up. Second, the AUL apparatus can be weighed before and after the test, and the difference in weight should nearly equal the weight of fluid picked up. A minimum of three tests are performed on a given sample and averaged to assign an AUL value.

EXAMPLES

The present invention is further illustrated by the following examples, which are not to be construed in any way as imposing limitations upon the scope thereof.

Blowing Agent Encapsulation

Sodium carbonate powder (FMC grade 50) is fluidized with heated air in a chamber. The coating solution, polyethylene glycol is aerosolized in the chamber and collides with the sodium carbonate particles in the vicinity of the aerosolizing nozzle. The temperature of the fluidizing air is adjusted to remove solvent and solidify the coating material shortly after colliding with the particles. The encapsulating solids adhere to the particle surface in the form of a film or coating. The encapsulating solid adheres to the particle surface in the form of a film or coating. This process is maintained until each particle is encapsulated to the prescribed film thickness. This process is also known as the Würster process.

SAP A

In a 1-gal plastic reaction vessel, 834.12 g of distilled water and 458.51 g of 50 wt. % aqueous sodium hydroxide were mixed together and cooled to 25° C. 196.67 g of acrylic acid was added to the mixture and again cooled to 25° C. A solution of an additional 393.33 g of acrylic acid, 1.84 g of polyethylene glycol monoallylether acrylate and 0.61 g ethoxylated trimethlylolpropane triacrylate were added, the mixture cooled to 15° C. followed by the addition of 21.94 g (50% wt/wt) methoxypolyethylene glycol monomethacrylate. This monomer mixture was cooled to approximately 5° C. and sparged with $N_2$ gas and then polymerized under adiabatic conditions by the addition of 130 ppm hydrogen peroxide, 150 ppm azo-bis-(2-amidino-propene) dihydrochloride, 200 ppm sodium persulfate and 48 ppm sodium erythorbate and held at $T_{max}$ for 20 minutes.

The polymerized gel was chopped and extruded with a Hobart 4680 commercial meat grinder, followed by drying in a Procter & Swartz Model 062 forced air oven at 175° C. for 10 minutes on a 20 in×40 in perforated metal tray with up flow and 6 minutes with the down flow to a finished product moisture level of approximately 3–5%. The dried material was coarse ground in a glass crusher, milled with an MPE three stage roller mill and sieved with a Minox screener to remove particles greater than about 850 μm and smaller than about 150 μm. The vortex time of the SAP particles was measured before surface crosslinking (PSXM Vortex). 400 g of sieved powder was coated with a solution of 1% ethylene carbonate, 4.0% water, 4.0% acetone, using a finely atomized spray from a Paasche VL airbrush while the SAP particles are mixed in a high intensity mixer. All wt. % values are based on the weight of dry SAP powder. The coated material was then heated for 25 minutes at 195° C. in a General Signal/BM OV-510A-3 forced air oven. After cooling, the resulting surfaced crosslinked SAP A was analyzed for tea bag retention capacity (TB), Vortex time (SX Vortex) and AUL(0.9 psi).

Examples 1 to 4

Examples 1–4 were produced using the method of making SAP A with the step that immediately, prior to the addition of initiators, 14.65 g of the encapsulated FMC grade 50 sodium carbonate was added to the monomer solution.

Encapsulated blowing agents for Examples 1–4 are as follows: example 1 used FAS C250, a 50% active coating of 2000 molecular weight polyethylene glycol; example 2 used FAS C270, a 70% active coating of 2000 molecular weight polyethylene glycol; and examples 3 and 4 used FAS C850 and FAS C870, which are a 50% and 70% active coating of polyethylene glycol 8000 molecular weight in the monomer solution respectively. Each encapsulated coating variant was applied to the surface of the FMC grade 50 sodium carbonate.

After surface crosslinking (SX), the resulting polymers in Examples 1–4 were analyzed for tea bag retention capacity (TB), Vortex time and AUL(0.9 psi).

TABLE 1

SAP A and Examples 1–4

| Examples | Encapsulated Blowing Agent | Active Coating % | PSXM Vortex (sec) | SX TB (g/g) | SX Vortex (sec) | 0.9 psi AUL (g/g) |
|---|---|---|---|---|---|---|
| SAP A | none | 0 | 45 | 30 | 85 | 21.0 |
| 1 | FAS C250 | 50 | 26 | 36.0 | 31 | 11.5 |
| 2 | FAS C270 | 70 | 22 | 34.0 | 28 | 20.0 |
| 3 | FAS C850 | 50 | 22 | 35.0 | 32 | 19.0 |
| 4 | FAS C870 | 70 | 22 | 38.0 | 31 | 12.3 |

Example 5 to 7

Examples 5–7 were produced using the same method of Examples 1–4 except 3.48 g of polyethylene glycol monoallylether acrylate, 0.29 g of ethoxylated trimethylolpropane triacrylate and 1.45 g hydroxypolyethoxy allyl ether were added to the monomer. Immediately prior to polymerization, 2 to 4 wt. % of the encapsulated blowing agent was added to the monomer solution, the amounts found in Table 2. Vortex times of Examples 1–4 were measured before surface crosslinking (PSXM Vortex). After surface crosslinking (SX), the resulting polymers in Examples 5–7 were analyzed for tea bag retention capacity (TB), Vortex time and AUL (0.9 psi).

TABLE 2

Examples 5–7

| Examples | % C270 | PSXM Vortex (sec) | SX TB (g/g) | SX Vortex (sec) | 0.9 psi AUL (g/g) |
|---|---|---|---|---|---|
| 5 | 2.0 | 24 | 31.5 | 31 | 20.7 |
| 6 | 3.0 | 15 | 29.7 | 20 | 22.0 |
| 7 | 4.0 | 16 | 31.2 | 21 | 20.4 |

SAP B

In a 5-gal plastic reaction vessel, 3423.37 g of distilled water and 1545.37 g of 50 wt. % sodium hydroxide were mixed together and cooled to 25° C. 773.33 g of acrylic acid was added to the mixture and cooled to 25° C. A solution of an additional 1547.67 g of acrylic acid, 9.28 g of polyethylene glycol monoallylether acrylate, 13.92 g of triallylamine were added, the mixture cooled to 5° C. and sparged with $N_2$ gas and then polymerized under adiabatic conditions by the addition of 130 ppm hydrogen peroxide, 200 ppm azo-bis-(2-amidino-propene) dihydrochloride, 800 ppm sodium persulfate and 50 ppm sodium erythorbate and held at $T_{max}$ for 20 minutes.

The polymerized gel was chopped and extruded with a Hobart 4680 commercial meat grinder, followed by drying in a Procter & Swartz Model 062 forced air oven at 175° C. for 10 minutes on a 20 in×40 in perforated metal tray with up flow and 6 minutes with the down flow to a finished product moisture level of approximately 3–5%. The dried material was coarse ground in a glass crusher, milled with an MPE three stage roller mill and sieved with a Minox screener to remove particles greater than 850 microns and smaller than 150 microns. The vortex time of the SAP particles was measured before surface crosslinking (PSXM Vortex). 400 g of sieved powder was coated with a solution of 1% ethylene carbonate, 4.0% water, 4.0% acetone, using a finely atomized spray from a Paasche VL airbrush while the SAP particles are mixed in a high intensity mixer. All wt. % values are based on the weight of dry SAP powder. The coated material was then heated for 25 minutes at 195° C. in a General Signal/BM OV-510A-3 forced air oven. After cooling, the resulting SAP B was analyzed for tea bag retention capacity (TB), Vortex time (SX Vortex) and AUL (0.9 psi).

Example 8 to 9

Examples 8–9 below were produced using the same method described for SAP B. Immediately prior to the addition of the initiators for polymerization, the encapsulated FMC grade 50 sodium carbonate in the amounts shown in Table 3 were added to the monomer solution. Vortex times of Examples 8 & 9 were measured before surface crosslinking (PSXM). After surface crosslinking (SX), the resulting polymers in Examples 8–9 were analyzed for tea bag retention capacity (TB), Vortex time and AUL(0.9 psi).

TABLE 3

SAB B and Examples 8–9

| Example | % C270 | PSXM Vortex (sec) | SX TB (g/g) | SX Vortex (sec) | 0.9 psi AUL (g/g) |
|---|---|---|---|---|---|
| SAP B | 0 | 52 | 30 | 110 | 21.0 |
| 8 | 4 | 23 | 24.5 | 17.5 | 22.7 |
| 9 | 5 | 20 | 24.1 | 17.9 | 22.7 |

The examples described for the process according to the invention all show a very good overall performance, in particular in respect to the relationship of tea bag retention, vortex time as set out in the example and AUL(0.9 psi).

What is claimed:

1. A superabsorbent polymer comprising a resin encapsulated blowing agent and having a vortex time of about 40 seconds or less wherein said resin is selected from natural or synthetic resins, acrylonitrile-butadiene rubbers, viscous settable ceramic materials, polyolefins, polyethylene gylcol, olefin copolymers, polyaromatic olefins, styrenic compounds or polymerized halo-diolefins, and wherein the resin encapsulated blowing agent provides a controllable delayed release of the blowing agent.

2. The superabsorbent polymer of claim 1 wherein the vortex time is about 32 seconds or less.

3. The superabsorbent polymer of claim 1 wherein the resin encapsulated blowing agent comprising a carbonate or compound thereof.

4. The superabsorbent polymer of claim 1 wherein the resin is polyethylene glycol.

5. The superabsorbent polymer of claim 1 having an AUL(0.9 psi) of about 10 g/g of more.

6. The superabsorbent polymer of claim 1 having a tea bag retention of about 20 g/g of more.

7. A superabsorbent polymer comprising:
   a) from about 55 to about 99.9 wt. % of polymerizable unsaturated acid group containing monomers;
   b) from about 0.001 to about 5.0 wt. % of internal crossliniking agent; wherein the composition has a degree of neutralization of more than about 20 mol %; and
   c) from about 0.05 to about 10.0 wt. % of a resin encapsulated blowing agent wherein said resin is selected from natural or synthetic resins, acrylonitrile-butadiene rubbers, viscous settable ceramic materials, polyolefins, olefin copolymers, polyaromatic olefins, styrenic compounds or polymerized halo-diolefins, and wherein the resin encapsulated blowing agent provides a controllable delayed release of the blowing agent.

8. The superabsorbent polymer of claim 7 wherein the resin encapsulated blowing agent comprising a carbonate or compound thereof.

9. The superabsorbent polymer of claim 7 wherein the resin is polyethylene glycol.

10. The superabsorbent polymer of claim 7 having a vortex time of about 40 seconds or less.

11. The superabsorbent polymer of claim 7 having a vortex time of about 32 seconds or less.

12. The superabsorbent polymer of claim 7 having a vortex time of about 20 seconds or less.

13. The superabsorbent polymer of claim 7 having an absorbency under load at 0.9 psi of about 10 g/g of more.

14. The superabsorbent polymer of claim 7 having a tea bag retention of about 20 g/g of more.

15. The superabsorbent polymer of claim 7 having a tea bag retention of about 24 g/g of more.

16. An absorbent article comprising a superabsorbent polymer comprising:
  a) from about 55 to about 99.9 wt. % of polymerizable unsaturated acid group containing monomers;
  b) from about 0.001 to about 5.0 wt. % of internal crossliniking agent; wherein the wherein the composition has a degree of neutralization of more than about 20 mol %; and
  c) from about 0.05 to about 10.0 wt. % of a resin encapsulated blowing agent wherein said resin is selected from natural or synthetic resins, acrylonitrile-butadiene rubbers, viscous settable ceramic materials, polyolefins, olefin copolymers, polyaromatic olefins, styrenic compounds or polymerized halo-diolefins, wherein the superabsorbent polymer has a vortex time of about 40 seconds or less, and wherein the resin encapsulated blowing agent provides a controllable delayed release of the blowing agent.

17. The superabsorbent polymer of claim 1 wherein the resin encapsulated blowing agent is a polyethylene glycol coated sodium carbonate.

18. The superabsorbent polymer of claim 7 wherein the resin encapsulated blowing agent is a polyethylene glycol coated sodium carbonate.

19. The absorbent article of claim 16 wherein the resin encapsulated blowing agent is a polyethylene glycol coated sodium carbonate.

* * * * *